United States Patent [19]

Franks

[11] Patent Number: 4,863,865

[45] Date of Patent: Sep. 5, 1989

[54] PRESERVATION BY COLD STORAGE

[76] Inventor: Felix Franks, 7, Wootton Way, Cambridge CB3 9LX, England

[21] Appl. No.: 213,517

[22] Filed: Jun. 28, 1988

Related U.S. Application Data

[63] Continuation of Ser. No. 644,505, Aug. 24, 1984, abandoned.

[30] Foreign Application Priority Data

Aug. 26, 1983 [GB] United Kingdom ............... 8323094

[51] Int. Cl.$^4$ .................. C12N 1/00; C12N 5/00; C12N 1/04; C12N 1/30
[52] U.S. Cl. ..................... 435/240.2; 435/240.4; 435/243; 435/250; 435/252.1; 435/254; 435/255; 435/256; 435/260
[58] Field of Search ............ 435/243, 254, 255, 260, 435/1, 2, 249, 250, 256, 240.2, 240.4, 252.1

[56] References Cited

U.S. PATENT DOCUMENTS

| | | | |
|---|---|---|---|
| 2,710,810 | 6/1955 | Strashun | 435/260 |
| 2,929,150 | 3/1960 | Johnston | 435/260 |
| 3,193,390 | 7/1965 | Champagnat et al. | 435/248 |
| 3,982,004 | 9/1976 | Obata et al. | 426/641 |
| 4,217,419 | 8/1980 | Suzuki | 435/253 |

FOREIGN PATENT DOCUMENTS

| | | | |
|---|---|---|---|
| 1449606 | 9/1976 | United Kingdom | 435/260 |

OTHER PUBLICATIONS

Pelczar, M. J., "Manual of Microbiological Methods", (McGraw-Hill, publishers 1957) p. 107.

Mackey, "Lethal and Sublethal Effect of Refrigeration, Freezing and Freeze-Drying on Microorganisms"; *The Revival of Injured Microbes*, Andrew e.d. Academic Press, London, (1984), pp. 45-75.

Zialoguev et al., "Preserving Agent for Microflora", *Chem. Absts.*, vol. 87 (1977), Abstract No. 2314a.

Kline et al., "New Technique of Kidney Tissue Processing for Immunoflourescence Microscopy: Formol Sucrose/Gum Sucrose/Paraffin", *Laboratory Investigation*, vol. 47(2), (1982) pp. 206-213.

Franks, "Preservation of Cells", *Chem. Absts.*, vol. 97 (1982), Absts. No. 178379.

Mathias et al., "Nucleation and Growth of Ice in Deeply Undercooled Erythrocytes", *Cryobiology*, vol. 21 (1984), pp. 123-132.

*Primary Examiner*—Elizabeth C. Weimar
*Attorney, Agent, or Firm*—Abelman Frayne Rezac & Schwab

[57] ABSTRACT

Material which contains water, or is accompanied by an aqueous phase, notably biological cells, cell components or cell aggregates, or differentiated biological tissue is preserved by dispersion in an oil medium and under-cooling the dispersion, preferably to a temperature in the range $-20°$ C. to $-40°$ C. The oil medium is characterized by the absence of surfactant which can catalyze ice formation and is an immobile gel at the storage temperature. The preferred oil 10 medium is paraffin oil, or oil plus paraffin wax.

15 Claims, No Drawings

PRESERVATION BY COLD STORAGE

This application is a continuation of application Ser. No. 644,505, filed Aug. 24, 1984, now abandoned. This invention relates to the preservation of material by storage at a low temperature. In particular, although by no means exclusively, the invention relates to the preservation of material which is of biological origin. It may be applied to the preservation of whole cells in a viable condition, so as to retain their ability to function and/or reproduce (if capable of reproduction) on return to normal temperature. It may be applied to the preservation of differentiated biological tissue in a viable condition so that it is able to grow when restored to normal temperature e.g. room temperature of about 20° C. However, the invention could conceivably be applied to the preservation of cell aggregates, or cell organelles from ruptured cells, or protoplasts, or isolated proteins, or the invention could be used to preserve cells or cell "ghosts" (membrane vesicles) in a useful but not fully viable condition.

The invention might also be applied to the preservation of materials which are not of biological origin. The invention is generally applicable to substances which contain an aqueous phase or are accompanied by an aqueous phase, but cannot withstand freezing of the water in the aqueous phase (at least in the absence of chemical additives). The materials to be preserved might be a substance dissolved or dispersed in water. In the case of biological cells or cell aggregates or cell organelles the aqueous phase will include intra-cellular water. In the case of differentiated biological tissue it will include intra-cellular water together with any extra-cellular water contained within the tissue.

The low temperature preservation of cells by this invention could be used as an alternative to maintaining cultures of cells with repeated subculturing and the concomitant possibility of propagating mutations. It could also be employed for the preservation of spermatozoa or blood components, or when it was desired to transport a cell culture or thermolabile material. A particular interest is in connection with the cloning of animal or plant cells or microorganisms.

The conventional technique for the low temperature preservation of biological cells is to freeze them and in some way ameliorate the destructive effect of freezing, notably by adjusting the cooling rate to control the rate of dehydration of the cells, and/or by including a cryoprotectant. Conventional cryoprotectants are dimethyl sulfoxide, ethylene glycol, and glycerol. This technique can only be applied to certain cells; moreover cryoprotectants can themselves be somewhat toxic, so exposing the cells to the chemical cryoprotectant is inherently undesirable. Cryoprotectants may well preserve a cell's biochemistry, but destroy a biological function such as its ability to reproduce or motility.

A possible alternative to freezing is to employ the phenomenon of undercooling (also known as supercooling) in which water is cooled below its normal freezing point without freezing taking place. Water droplets, if small enough, can be undercooled to around −40° C., when ice formation inevitably occurs. Undercooling to lower temperatures is possible if dissolved additives are present. Undercooling to around −10° C. can occur in nature. However, undercooling has received very little attention as a storage/preservation technique. There has been only limited investigation in the area, and there are some conflicts of views as to the mechanism of freezing of undercooled cells and as to whether exposure to cold is per se harmful even if freezing is prevented.

D. H. Rasmussen, M. N. Macauley, A. P. Mackenzie "Supercooling and Nucleation of Ice in Single Cells Cryobiology 12 328–339 (1975) describes the undercooling of erythrocytes suspended in heptane, and yeast cells suspended in safflower oil, with a surfactant present in each case to assist formation of a water in oil emulsion. No intact erythrocytes could be recovered. while it was found that the yeast cells were dying at a rate which was observable at −20° C. and was greater at lower temperatures. The authors of that paper could not account for the death of the yeast cells. The surfactant used was sorbitan tristearate which is one of the few surfactants promoting formation of water-in-oil emulsions.

The present inventor and co-workers have published the results of investigations into the undercooling of cells suspended in silicone oil, with the surfactant sorbitan tristearate present to enable emulsion formation (F. Franks and M. Bray, Cryo-Letters 1, 221–226, 1980; F. Franks, S. F. Mathias, P. Galfre, S. D. Webster and D. Brown, Cryobiology 20 298–309, 1983). They found that freezing of cells occurred at above the temperature (around −40° C.) at which spontaneous freezing would be inevitable, a result which contradicts an opposite finding by Rasmussen et al.

P. M. Zavos and E. F. Graham, Cryobiology 18 497–505 (1981) describes endeavours to preserve turkey sperm emulsified in silicone oil. Some of the emulsions did not include a surfactant but did include cryoprotectants, and were formed by means of a special technique (of which full details were not given). This gave relatively large droplets, many of them having sizes in excess of 100 μm.

They found that sperm stored in emulsion at −21° C. for one hour displayed somewhat reduced motility. The published paper does not mention other storage periods or storage at lower temperatures. Emulsified sperm which was not undercooled displayed an average motility of 79.2%, and undercooling to −21° C. for 1 hour reduced this to 55.0% i.e. 70% of the control. Rasmussen et al reported a survival level of around 80% (but decreasing as mentioned above) for yeast cells undercooled to −20° C. for 6 to 7 hours, and much lower survival rates at −25° C. and below.

These prior workers have not been able to keep an aqueous emulsion phase undercooled but unfrozen overnight.

The Zavos and Graham paper also reported that some droplets froze at around −18° C., but the majority undercooled to about −43° C. However, no distinction was made between droplets containing sperm and droplets containing none, and it seems likely that large droplets containing sperm were freezing at −18° C., whereas those undercooled to −43° C. were small droplets which did not contain sperm. Moreover these droplets contained cryoprotectant.

According to a first aspect of the present invention there is provided a method of preserving material containing or accompanied by an aqueous phase, and which cannot withstand freezing of the water thereof which comprises dispersing the material in an oil medium and cooling the dispersion to a storage temperature such that the aqueous phase is undercooled, characterised in that (i) surfactant capable of catalyzing ice formation is absent, and (ii) the said oil medium is a pourable liquid when the dispersion is made but is immobile at the storage temperature.

The invention also includes in one further aspect, a dispersion of material in an oil medium which is a pourable liquid at 20° C but becomes immobile on cooling to a temperature which is above the freezing point of the aqueous phase. In a yet further aspect the invention includes material preserved by the method of the invention.

The absence of surfactant has been found essential for storage over an extended period. The inventor has found that surfactant undergoes a slow transformation which renders it effective as a catalyst for ice nucleation, thus rendering the emulsion liable to freezing. This explains the poor survival rate found by Rasmussen et al.

Use of an oil medium which becomes immobile on cooling is beneficial, in that it inhibits the diffusion of droplets within the dispersion and hence inhibits coalescence of them into large droplets which would have a greater tendency to freeze. (The extent to which undercooling can be achieved is inversely dependent on the volume of the dispersed aqueous droplets).

Such a medium is quite distinct from heptane or silicone oil as used previously, because heptane or silicone oil have viscosities which are largely independent of temperature, and do not gel in the temperature range of interest (0° C. down to about −40° C.). Preferably the oil medium gels not lower than −20° C., and it may gel at an even higher temperature.

With this invention it has been found unnecessary to include any cryoprotectant, and it is strongly preferred that such material should be absent also.

It can be desirable to employ an oil medium which gels only a little (say 15°-20° C. or less) below the temperature at which the dispersion is made.

One possibility is for the dispersion to be formed at a temperature of 0° to 10° C., notably at about 4° C., with an oil medium which gels not lower than −20° C. Glycerides can provide such an oil medium, and it has been found that use of a glyceride as the oil medium gives results which are an improvement over the prior art.

Sunflower oil for instance is pourable, and indeed quite mobile, at 4° C. but at −10° C. it has a similar consistency to honey and it gels at about −18° C. It is a triglyceride and generally contains 12-% of saturated carboxylic acids, the remainder being oleic and linoleic acids whose relative proportions vary with the origin of the sunflower oil.

It has however been found that some crystallization and ice formation does eventually occur with sunflower oil. It is preferred to utilize a paraffin which gels at a temperature in the range from −20° C. to +20° C., A commercially available paraffin which has been found satisfactory is a heavy paraffin oil, Specific Gravity 0.86-0.89 from Fisons Ltd., Loughborough, England. This oil displays viscosities of:

| 0.18 | Pascal. sec | at 20° C. |
| 0.3 | Pascal. sec | at 8° C. |
| 1.6 | Pascal. sec | at −7° C. |
| 10.7 | Pascal. sec | at −19° C. |

With this oil it is possible to form, at room temperature, a stable emulsion capable of undercooling to −40° C.

A yet further improvement resides in the use of a mixture of paraffin oil with paraffin wax which itself is immobile at 20° C. I have found that such mixtures form suitable immobile gels (although these can be broken up by the shear forces of shaking) and the gel temperature can be adjusted by varying the proportions of oil and wax in the mixture.

The gel itself contains crystallinity, as evidenced by liberation of latent heat as it solidifies, yet it does not catalyze ice nucleation even down to −40° C.

With a paraffin oil and wax mixture the mixture may become immobile at a temperature not lower than 0° C. and preferably it is arranged to become immobile at a temperature not lower than 10° C.

A further unexpected advantage of paraffin oil or oil/wax mixtures is an observation that there is less damage to cells during the emulsification procedure.

A suitable wax is paraffin wax with a congealing point of 45° C. available from East Anglia Chemicals, Halstead, Suffolk, England.

According to a further aspect of this invention there is provided a method of preserving material comprising dispersing the material in paraffin oil, or a mixture of paraffin oil and paraffin wax, and cooling the dispersion to a storage temperature such that an aqueous phase contained in or accompanying the material is undercooled, the oil or oil/wax mixture being a pourable liquid which is immobile at the storage temperature.

Whatever oil is used in this invention, it is preferred that it should not be a drying oil. In general particulate materials act as a catalyst for ice nucleation. Consequently, it is preferred to avoid oils which crystallize. However, paraffin wax has been found to be an exception which does not catalyze ice nucleation, as mentioned above.

To avoid crystallisation when glycerides are used it is preferred to have a fairly broad range of fatty acid chain lengths present. Thus sunflower oil is preferred over safflower oil which displays substantially greater drying properties, and over olive oil which crystallizes, presumably because of its high proportion of oleic acid residues and indeed of triolein.

For this invention a dispersion of biological cells in the oil can be made using a conventional laboratory homogenizer such as a polytron coaxial cylinder homogenizer.

The cells may be separated from almost all of a liquid aqueous medium by centrifuging, followed by suspending the material of the centrifuged pellet (i.e. the cells and a small amount of extra-cellular solution) in the oil medium by means of the homogenizer.

In this way it has been found possible to obtain dispersion of erythrocytes in which the disperse phase is clusters of individual erythrocytes - the mean was 16 - closely packed in a small amount of extracellular aqueous solution calculated to be in the region of 20 $\mu m^3$, but depending somewhat on the number of erythrocytes in the clusters. There were cells in all the droplets, i.e. none of them contained extra-cellular aqueous medium only, and the volume of intra-cellular water substantially exceeded the small amount of extra-cellular water.

When the stored material is biological cells, cell organelles or cell aggregates it is preferred that the amount of intra-cellular water exceeds the amount of extra-cellular water in the disperse phase. When the stored material is differentiated biological tissue it is strongly preferred that the amount of water contained in the biological tissue (intra-cellular water together with any extra-cellular water in the tissue) is in an excess over the amount of any other water surrounding the tissue and present with it in the disperse phase.

Once the dispersion in the oil medium has been formed (using a pre-chilled oil medium if it is desired to form the dispersion below room temperature) it is cooled to the storage temperature and held at that temperature. The cooling can be effected by means of a cooling bath of liquid. Storage could be in this but it is more convenient to store in a deep freeze. Cooling can also be effected by simply placing the dispersion in deep freeze.

For some species I have found that uncontrolled rapid cooling does damage (a cold shock) even though there is no freezing. For such species controlled cooling at about one third of a degree per minute avoids the harmful cold shock.

The storage temperature may be selected with regard to the particular species, since some can be cooled to lower temperatures than others. For example erythrocytes can be cooled to $-30°$ C. whereas cultured soya bean cells cannot be taken below about $-25°$ C. because they contain catalytic sites which nucleate intracellular ice formation below this temperature.

After storage for the desired time the stored material can be recovered by warming to a temperature above $0°$ C. (possibly around $4°$ C., possibly room temperature), breaking the dispersion and separating the material. The dispersion may be broken by addition of an isotonic aqueous solution, after which the aqueous phase containing the cells or other stored material is separated from the oil. If desired, stored biological cells may be centrifuged out of this aqueous phase, and resuspended in more of it, as a washing operation.

EXAMPLES

In general for these Examples, glassware, water and growth medium were sterilized before use, by autoclaving under 1 bar superatmospheric pressure for 15 minutes. The paraffin oil and wax were the Fisons heavy paraffin oil and the East Anglia Chemicals paraffin wax mentioned above.

EXAMPLE 1

Suspension cooling and recovery of yeast (*Saccharomyces cerevisiae*) using sunflower oil A. Preparation of yeast cells 10 mls actively growing yeast suspension (in a sterile glucose rich medium*) was centrifuged at 400 g for 5 minutes. Yeast cells formed a pellet at the bottom of the centrifuge tube. The supernatant medium was removed with a sterile pipette and replaced with 10 ml sterile distilled water. The yeast was thoroughly resuspended and spun again at 400 g for 5 minutes. 9 ml of the supernatant water were removed with a sterile pipette, and the yeast cells resuspended in the remaining 1 ml water, ready for use in an emulsion.

B. Preparation of yeast in sunflower oil emulsion 10 ml sunflower oil in a plastic vial, the 1 ml prepared yeast cells (para. A above) in a centrifuge tube, several small plastic screw topped ampoules, a sterile 1 ml graduated plastic syringe and a sterile pasteur pipette were all pre-cooled in ice.

Emulsification was carried out with a "polytron" homogenizer, operating at a speed of 6000 rpm. The homogenizer's head was dipped in alcohol and allowed to dry before use to maximise sterility. The homogenizer's head was immersed in the pre-cooled sunflower oil and the yeast suspension was added drop wise with the pasteur pipette while the homogenizer was running. The agitation of the oil ensured that the yeast cells were rapidly and evenly dispersed in small droplets throughout the oil. It is necessary to cool the oil (such as by prior cooling in ice, as done here) to counter the heating effect of the homogenizer so that the mobility of the oil remains low and a stable emulsion is produced. When all the yeast cells had been added to the oil (approx. 1 minute) the homogenizer was switched off and the emulsion replaced in the ice bucket. 1 ml aliquots of emulsion were put into each of the pre-cooled plastic ampoules with the 1 ml graduated syringe and the tops screwed down tightly. One ampoule was retained to be used as "control", the others were quickly transferred to a cooling bath containing stirred ethylene glycol 5 at $-30°$ C. Yeast cells in the control sample were recovered and assessed for survival as described in paragraph C. Yeast cells in the "control" sample underwent all the experimental procedures except cooling, so that an assessment of the control sample shows any damage to the cells caused by the emulsification and recovery from emulsion. Samples from the cooling bath were removed after 1, 2, 4 and 6 hours and left to attain room temperature before the cells were recovered and survival assessed.

C. Recovery of yeast cells and assessment for survival

The 1 ml emulsion sample was poured into a sterile centrifuge tube. 10 ml sterile distilled water were added and the two phases mixed as well as possible by shaking. The excess of aqueous phase destabilize the emulsion. The mixture was centrifuged at 400 g for 5 minutes after which time the yeast cells had rejoined the aqueous phase and formed a pellet at the bottom of the tube. The viscous oil layer on the surface of the water was removed with a sterile pipette, together with 9 ml of the water. The yeast cells were resuspended in the remaining 1 ml water and transferred to a bottle containing 99 ml sterile distilled water. After thorough mixing, a sample of the yeast suspension was taken with a sterile pasteur pipette and the number of yeast cells per ml counted using a haemocytometer slide. Further dilutions of the yeast suspension were made with sterile distilled water until a concentration of approximately $10^3$ cells per ml was reached.

0.1 ml of this yeast suspension was dispensed onto each of four 9cm sterile plastic petri dishes containing 20 ml glucose rich medium solidified with agar. The suspension was spread on the surface of the agar with a sterile glass spreader. The plates were sealed with Nesco film and stored at $+25°$ C. for 48 hours. The number of yeast colonies per plate was then counted, and compared with the number of yeast cells per ml before cooling, which had been counted by haemocytometer slide.

D Results

| Cells per ml (H'cytometer before cooling) | Hours at −30° C. | Cells per ml (plate count after cooling) | % survival |
| --- | --- | --- | --- |
| $1.3 \times 10^6$ | 0 (control) | $1.0 \times 10^6$ | 77 |
| $1.4 \times 10^6$ | 1 | $1 4 \times 10^6$ | 100 |
| $1.3 \times 10^6$ | 2 | $1.0 \times 10^6$ | 77 |
| $1.3 \times 10^6$ | 4 | $0.9 \times 10^6$ | 70 |
| $1.3 \times 10^6$ | 6 | $1.3 \times 10^6$ | 100 |

For comparison yeast cells were suspended in distilled water, cooled and stored at −30° C. for 6 hours, 10% survived.

This Example could alternatively be performed without resuspending the centrifuged pellet in 1 ml of water at the end of para. A, and suspending that pellet directly in the Sunflower oil.

| *Glucose rich medium, to make 1 liter | |
| --- | --- |
| Yeast extract | 10 g |
| Bactopeptone | 20 g |
| Glucose | 20 g |
| Adenine | 20 mg |
| plus Bacto agar | 20 g if required |

EXAMPLE 2

Suspension, cooling and recovery of yeast (*saccharomyces cerevisiae*) using paraffin oil

A. Preparation of yeast cells 10 ml actively growing yeast suspension in the same sterile glucose rich medium was concentrated in 0.5ml of water by the procedure of Example 1A.

B. Preparation of yeast in paraffin oil emulsion

The 0.5 ml of prepared yeast cells was emulsified in 10 ml of paraffin oil and 1 ml aliquots of emulsion were put into plastic ampoules. The procedure was exactly as described in Example 1 part B except that no cooling or pre-cooling was needed.

One ampoule was retained to be used as "control", the others were quickly transferred to a freezer compartment at −20° C. Yeast cells in the control sample were recovered and assessed for survival as described in paragraph C. Yeast cells in the "control" sample underwent all the experimental procedures except cooling, so that an assessment of the control sample shows any damage to the cells caused by the emulsification and recovery from emulsion. Samples from the freezer were removed after 4, 8 and 12 weeks and left to attain room temperature before the cells were recovered and survival assessed.

C. Recovery of yeast cells and assessment for survival

The procedure of Example 1 part C was employed except that the number of yeast colonies per plate was compared with the number of yeast cells per ml recovered. These had been counted by haemocytometer slide, so as to count both viable and dead cells.

D. Results

| Cells per ml recovered (H¹'cytometer) | Weeks at −20° C. | Cells per ml alive (plate count) | % survival |
| --- | --- | --- | --- |
| $2.4 \times 10^6$ | 0 (control) | $1.5 \times 10^6$ | 63 |
| $1.6 \times 10^6$ | 4 | $1.0 \times 10^6$ | 64 |
| $2.0 \times 10^6$ | 8 | $1.3 \times 10^6$ | 66 |
| $1.9 \times 10^6$ | 12 | $1.2 \times 10^6$ | 64 |

For comparison yeast cells were suspended in distilled water, cooled and stored at −20° C. for 1 week: 10% survived.

EXAMPLE 3

Suspension, cooling and recovery of red blood cells,

A. Preparation of red blood cells

Fresh red blood cells (RBCs) were washed in phosphate buffered saline Dulbecco A (Oxoid Ltd). Washing was carried out by thoroughly mixing 1 ml concentrated RBCs with 9ml phosphate buffered saline (PBS) in a glass centrifuge tube and spinning at 400 g in a bench centrifuge.

The RBCs formed a pellet at the bottom of the tube. The supernatant was removed with a pasteur pipette and the RBCs resuspended in a fresh 9 ml PBS. When washing was completed (4 changes of PBS), as much as possible of the supernatant PBS was removed not more than 4 days.

B. Preparation and cooling of RBCs in sunflower oil emulsion 10 ml sunflower oil in a plastic vial, 1 ml washed RBCs in a small vial, small plastic screw topped ampoules, a 1ml graduated plastic syringe and a pasteur pipette were all cooled in an ice bucket.

Emulsification was carried out with a "polytron" homogenizer operating at its slowest setting. The homogenizers head was placed in the cooled sunflower oil, the homogenizer's was switched on, and the RBCs were added dropwise with the pasteur pipette. The agitation of the sunflower oil by the homogenizer ensured a rapid and even dispersal of the RBCs into small droplets throughout the oil. As in Example 1 it was necessary to cool the components of the emulsion to counter the heating effect of the homogenizer.

When all the RBCs had been added to the oil (approx. 1 minute) the homogeniser was switched off and the emulsion replaced in the ice bucket. 1 ml aliquots of emulsion were put into each of the pre-cooled plastic ampoules. One ampoule was retained to be used as a "control", the others were quickly transferred to a cooling bath (FTS Corporation, New York) containing stirred ethylene glycol at −25° C. RBCs from the "control" sample were recovered and assessed for survival as described below. RBCs in the "control" sample undergo all the experimental procedures except cooling so tat assessment of the control sample shows the amount of damage to the cells caused by the emulsification and recovery from emulsion. Samples from the cooling bath were removed after 6 days, and left to attain room temperature before the cells were recovered and survival assessed exactly as for the control sample.

C. Recovery of RBCs from emulsion and assessment for survival

The 1 ml emulsion sample was poured into a centrifuge tube. 10 mls PBS was added and the two phases mixed as well as possible by gentle shaking. The excess of aqueous phase destabilized the emulsion.

This mixture was centrifuged at 400 g for 5 minutes, after which time the RBCs had rejoined the aqueous phase and formed a pellet at the bottom of the tube. The PBS was tinged pink, due to the RBCs which had been damaged during the experiment and had lysed, releasing their haemoglobin into the PBS. After removal by pipette of the viscous oil layer on the surface, the pink PBS was pipetted into a glass cuvette and the optical density of the solution at 540 nm read on a spectrophotometer and recorded. Any remaining pink PBS was removed from the RBCs in the centrifuge tube, and 10 ml fresh PBS added, and the RBCs resuspended thoroughly. This suspension was again centrifuged at 400 g for 5 minutes, when the RBCs had again formed a pellet at the bottom of the tube and the PBS was faintly pink. The optical density at 540 nm of this solution was determined as above. When all the PBS had again been removed from the RBC pellet, 10 ml distilled water +1 drop detergent were added to the pellet and mixed thoroughly. This procedure caused the cells to lyse and destroyed the membranes so that a clear pink solution was obtained. The optical density of this solution was determined as described above. The quantity of intact cells in the sample was then calculated.

D. Repetition using paraffin oil

The procedure of parts A, B and C of Example 3 was followed, except that only 0.5 ml of washed RBCs was suspended in 10 ml of paraffin oil (by the procedure of Part B). Pre-cooling, and cooling during dispersion were not needed. Samples were kept in the cooling bath at $-+°$ C. for 3 weeks. In the recovery step, part C, the destabilized emulsion was centrifuged at 1000 g for 15 minutes to separate the RBCs and aqueous phase from the paraffin oil.

E. Results

| Optical Densities at 540 nm | | | |
|---|---|---|---|
| with sunflower oil | | with paraffin oil | |
| Control | Sample | Control | Sample |
| 6 days at $-25°$ C. | | 3 weeks at $-30°$ C. | |
| a: 0.198 | 0.557 | 0.964 | 0.980 |
| b: 0.141 | 0.240 | 0.089 | 0.042 |
| c: 1.397 | 0.964 | 7.630 | 3.512 |
| Proportion of Intact Cells | | | |
| 80% | 55% | 88% | 77% | a = supernatant PBS after emulsion was broken
b = second PBS supernatant after "washing" cells
c = cells lysed with distilled water and detergent OD is proportional to concentration over this range. The aqueous solutions whose OD was measured were all 10 ml. Consequently the proportions of intact cells stated above are calculated as:

$$\% \text{ intact cells} = \frac{OD(c)}{OD(a) + OD(b) + OD(c)} \times 100\%$$

The intact cells are those which survive emulsification in the control, and emulsifications, cooling and storage in the sample, respectively. The quantity of intact cells in the sample, as a proportion of those in the control, is the proportion which survive cooling and storage. With sunflower oil, storing for 6 days at $-25°$ C. this was $$55/88 \times 100\% = 69\%$$

with paraffin oil, storing for 3 weeks at $-30°$ C., this was $$77/88 \times 100\% = 88\%$$

Non-emulsified RBC's suspended in PBS and stored at $-25°$ C. for 6 days, or at $-30°$ C. for 3 weeks, did not survive.

EXAMPLE 4

Suspension, cooling and recovery of sainfoin cultured cells *Onobrychis viciifolia* with paraffin oil (sainfoin is a forage plant. Cells of it were here cultured as undifferentiated single cells).

A. Preparation of cultured cells 5 ml cell suspension culture in sterile medium, 7 days after subculture, were spun at 400 g for 3 minutes in a bench centrifuge. Sainfoin cells formed a pellet at the bottom of the tube. The supernatant medium was removed with a sterile pipette.

B. Preparation of sainfoin cell in paraffin oil emulsion 10 ml paraffin oil was measured into a plastic vial. Emulsification was carried out with a "polytron" homogenizer operating at its lowest speed. Its head was dipped in alcohol and allowed to dry before use to maximise sterility. Approximately 1 g sainfoin cells, largely free from growth medium (see paragraph A) was transferred to the oil with the aid of a sterile spatula. The head was then immersed in the paraffin oil and the homogenizer switched on. After 15 seconds the agitation of the oil had been sufficient to disperse the cells in small clusters throughout the oil, and the homogenizer was switched off. The emulsion was divided into three aliquots in sterile polythene tubes with tight-fitting lids. Two aliquots were quickly transferred to a cooling bath filled with ethylene glycol and set at $-10°$ C. From the remaining aliquot the cells were recovered and assessed for survival (see paragraph C), so that any damage from the emulsification/recovery process could be estimated. Aliquots from the cooling bath were removed after 1 and 2 hours and left to attain room temperature before the cells were recovered and survival assessed.

C. Recovery of sainfoin cells and assessment of survival

The emulsion sample was poured into a sterile centrifuge tube. 10 ml sterile growth medium was added and the two phases mixed by gentle shaking. The excess of aqueous phase destabilized the emulsion. The mixture was centrifuged at 400 g for 5 minutes, after which time most of the sainfoin cells had rejoined the aqueous phase, and formed a pellet at the bottom of the tube. The viscous oil layer plus 9 mls of aqueous medium were removed with a sterile pipette. The cells were collected in a sterile pasteur pipette, and transferred to a 5 cm petri dish containing 5 mls sterile growth medium solidified with agar.* Survival was assessed by observation of growth of sainfoin colonies during incubation at 25° C.

D. Results

| Treatment | | Observed regrowth of cells after treatment |
|---|---|---|
| Control (see paragraph B) | | Yes |
| −10° C. | 1 hour | Yes |
| −10° C. | 2 hours | Yes |

*Growth medium for sainfoin cells after Uchimaya, H. and Murashige, T. Plant Physiology 57, 424–429 (1976).

EXAMPLE 5

Suspension, cooling and recovery of potato shoot-tips, *Solanum tuberosum* cv Maris Bard

A. Preparation of shoot-tips

Leafy shoots from potato tubers were cut into segments and leaves removed to reveal axillary buds. Segments were surface sterilized in a 10% (v/v) solution of domestic bleach for 10 minutes and then washed four times with sterile distilled water. Shoot-tips were dissected under a binocular microscope using sterile hypodermic needles to cut away unwanted leaflets and leaf primordia until the apical dome plus two to three primordia was left. This was excised and placed on sterile filter paper soaked with growth medium* and enclosed in a sterile petri dish. Shoot-tips prepared in this way were incubated at 25° C for 24 hours before use.

B. Suspension of shoot-tips in paraffin oil

Shoot tips were picked up on a sterile hypodermic needle and transferred to a sterile polythene vial containing 1 ml paraffin oil. One or two shoot tips were put in each vial, then transferred to a cooling bath containing ethylene glycol, preset to −10° C. The same procedure was repeated, using a 10:1 (v/w) mixture of paraffin oil and paraffin wax as the oil medium. Before use this mixture was heated gently to melt the wax and give a homogenous liquid, which was allowed to cool to room temperature.

Several shoot tips were placed in paraffin oil but left at 25° C. rather than −10° C., and several were taken from the filter paper (paragraph A) and placed directly in sterile tubes containing growth medium for assessment of growth (control treatment without cooling).

C. Recovery of potato shoot-tips and assessment of survival

Shoot-tips in the oil medium were removed from the cooling bath and left to attain room temperature. Shoot tips were picked out of the oil with a sterile hypodermic needle and placed on a filter paper support in a tube containing sterile growth medium, and incubated at 25° C.

D. Results

| Treatment | Number of shoot-tips in treatment | Number of shoot-tips growing on |
|---|---|---|
| Control (see paragraph B) | 5 | 5 |
| Oil alone at 25° C. 24 hours | 3 | 0 |
| Oil alone at −10° C. 24 hours | 5 | 5 |
| Oil + wax at −10° C. 48 hours | 4 | 2 |

*Growth medium for potato shoot-tips was Murashige and Skoog salts (ex. Flow Labs) plus
30: g/l sucrose
1.0: mg/l benzylaminopurine
0.05: mg/l α-naphthalene acetic acid Shoot tips were also frozen in growth medium for 24 hours at −10° C. None survived.

EXAMPLE 6

Suspension, cooling and recovery of pea shoot-tips, *Pisum sativum* cv Feltham First

A. Preparation of shoot-tips

Shoots were cut from pea seedlings which had been germinated under sterile conditions, 7 days after shoot emergence. Shoot-tips were dissected under a binocular microscope and incubated on growth medium* as in Example 5, paragraph A.

B. Suspension of shoot-tips in paraffin oil/wax mixture

A mixture of paraffin oil and paraffin wax (10:1 v/w) was heated gently until the wax melted and the mixture became homogeneous, then allowed to cool to room temperature before use. Shoot-tips were suspended nn the oil/wax mixture as in Example 5 paragraph B and transferred to a cooling bath containing ethylene glycol preset to −10° C. A few shoot-tips were placed directly in sterile tubes containing growth medium after the initial incubation of para A for assessment of growth (control treatment without cooling).

C. Recovery of pea shoot-tips and assessment of survival

As in Example 5 paragraph C.

D. Results

| Treatment | Number of shoot-tips in treatment | Number of shoot-tips on growing |
|---|---|---|
| control (no oil and wax | 3 | 1 |
| Oil and wax at −10° C. 24 hours | 3 | 3 |
| Oil and wax at −10° C. 48 hours | 4 | 3 |

*Growth medium for pea shoot-tips was Gamborg's B5: Gamborg O. L., R. A. Miller and K. Ojima Exp. Cell. Res. 50, 151–158 (1968).

What I claim and desire to secure by Letters Patent is:

1. A method of cold storing material selected from the group consisting of protoplasts and biological cells other than cells aggregated as tissue, said material comprising an aqueous phase and said method avoiding damage to said material which occurs upon freezing of said aqueous phase, which method comprises dispersing the material in an oil medium and subjecting the dispersion to a sequence of steps comprising cooling the dispersion to a storage temperature which is in a range from below 0° C. to −40° C. and also is such that said aqueous phase is under-cooled but without freezing thereof, storing the dispersion at said storage temperature, and subsequently returning the dispersion to a temperature above 0° C. to recover the preserved material, said sequence being carried out without cooling the dispersion sufficiently below said storage temperature to freeze the aqueous phase, cryoprotectants on additives capable of catalyzing ice formation being absent, and said oil medium being a pourable liquid when said dispersion is made but being an immobile gel at said storage temperature.

2. A method according to claim 1, wherein said intracellular water in said material dispersed in said oil medium is present in an amount which exceeds the amount of extra-cellular water present in said dispersion.

3. A method according to claim 1 wherein said storage temperature is not above −20° C. and said oil medium gels so as to become immobile at a temperature not lower than −20° C.

4. A method according to claim 1 wherein said oil medium is a paraffin oil.

5. A method according to claim 1 wherein said oil medium is a mixture comprising a paraffin oil which is mobile at 20° C. and a paraffin wax which is immobile at 20° C., said mixture being mobile at 20° C. but becoming an immobile gel at a temperature not lower than 0° C.

6. A method according to claim 5 wherein said mixture becomes an immobile gel at not lower than 10° C.

7. A method according to claim 1 wherein said material is a single cell organism and said storage temperature is not above −25° C.

8. A dispersion at a storage temperature in a range from below 0° C. to −40° C., comprising an oil medium and a dispersed material selected from the group consisting of protoplasts and biological cells other than cells aggregated as tissue, which material comprises an aqueous phase and is subject to damage upon freezing of said aqueous phase cryoprotectants on additives capable of catalyzing ice formation being absent, and said oil medium being a liquid which transforms from a pourable state to become immobile on cooling to a temperature which is above the freezing point of said aqueous phase, said aqueous phase being undercooled at said storage temperature, but without freezing thereof.

9. A dispersion according to claim 8 wherein said dispersed material contains intracellular water in an amount which exceeds the amount of extra-cellular water present in said dispersion.

10. A dispersion according to claim 1 wherein said oil medium is a paraffin oil.

11. A dispersion according to claim 8 wherein said oil medium is a mixture comprising a paraffin oil which is mobile at 20° C. and a paraffin wax which is immobile at 20° C., said mixture being mobile at room temperature but immobile at 0° C. and below.

12. A dispersion according to claim 11 wherein said mixture is immobile at 10° C. and below.

13. A dispersion according to claim 8 refrigerated to a temperature not above −10° C.

14. A dispersion according to claim 11 refrigerated to a temperature not above −10° C.

15. A dispersion according to claim 8 wherein said oil medium is a pourable liquid at 20° C.

* * * * *